United States Patent
Hecker et al.

(10) Patent No.: US 11,230,735 B2
(45) Date of Patent: Jan. 25, 2022

(54) SYSTEMS AND METHODS FOR CHARACTERIZING SEPSIS

(71) Applicant: ARIZONA BOARD OF REGENTS ON BEHALF OF THE UNIVERSITY OF ARIZONA, Tucson, AZ (US)

(72) Inventors: Louise Hecker, Tucson, AZ (US); Marvin J. Slepian, Tucson, AZ (US); Christian Bime, Tucson, AZ (US); Tong Zhou, Tucson, AZ (US); Ting Wang, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 16/065,360

(22) PCT Filed: Dec. 23, 2016

(86) PCT No.: PCT/US2016/068487
§ 371 (c)(1),
(2) Date: Jun. 22, 2018

(87) PCT Pub. No.: WO2017/112921
PCT Pub. Date: Jun. 29, 2017

(65) Prior Publication Data
US 2019/0276889 A1  Sep. 12, 2019

Related U.S. Application Data
(60) Provisional application No. 62/387,580, filed on Dec. 24, 2015.

(51) Int. Cl.
*C12Q 1/6883* (2018.01)
*C12Q 1/6886* (2018.01)
(Continued)

(52) U.S. Cl.
CPC ......... *C12Q 1/6883* (2013.01); *C12Q 1/6886* (2013.01); *G01N 33/6893* (2013.01);
(Continued)

(58) Field of Classification Search
CPC ............ C12Q 1/6883; C12Q 2600/158; C12Q 2600/118; C12Q 2600/112; C12Q 1/689;
(Continued)

(56) References Cited

U.S. PATENT DOCUMENTS

| | | | | |
|---|---|---|---|---|
| 2013/0288276 A1* | 10/2013 | Matsuya | ............ | G01N 33/6893 435/7.92 |
| 2014/0045915 A1* | 2/2014 | Skog | .................... | C12Q 1/6886 514/44 A |

(Continued)

FOREIGN PATENT DOCUMENTS

WO   2013/022995   2/2013

OTHER PUBLICATIONS

Casserly, B et al. 2011 Multimarker Panels in Sepsis. Crit Care Clin. vol. 27 p. 391-405.*

(Continued)

*Primary Examiner* — Mary K Zeman
(74) *Attorney, Agent, or Firm* — Venable LLP; Keith G. Haddaway; Daniel M. Podgorski

(57) ABSTRACT

The present disclosure relates to methods of characterizing disease. In particular, this invention relates to methods for selecting a treatment, treating, and predicting survival time in subjects suffering from sepsis, based on the characterization of genes associated with a reactive oxygen species (ROS) molecular signature.

8 Claims, 6 Drawing Sheets
(3 of 6 Drawing Sheet(s) Filed in Color)

(51) Int. Cl.
  *G01N 33/68* (2006.01)
  *G16B 40/00* (2019.01)
  *G16B 40/20* (2019.01)
(52) U.S. Cl.
  CPC ............. *G16B 40/00* (2019.02); *G16B 40/20* (2019.02); *C12Q 2600/106* (2013.01); *C12Q 2600/118* (2013.01); *C12Q 2600/158* (2013.01); *G01N 2800/26* (2013.01); *G01N 2800/52* (2013.01)
(58) Field of Classification Search
  CPC ........ C12Q 2537/165; C12Q 2600/106; C12Q 1/6816; C12Q 1/6895; C12Q 1/686; C12Q 1/04; G01N 2800/26; G01N 33/56911; G01N 33/569; G01N 2800/50; G01N 2800/52; G01N 2800/56; G01N 2800/60; Y02A 90/26; G16H 50/30; G16H 50/20; G16H 10/40; G16H 50/70; G16H 10/60; G16H 10/20; G16H 50/80; G16H 70/20; G16H 15/00; G16H 70/60; G16H 50/50; G16H 20/00; A61P 31/04; G06N 20/10; G06N 20/20; G06N 3/08; G06N 7/005; C40B 40/06; C40B 40/08; G16B 25/00; G16B 25/10; G16B 40/00; G16B 40/20; G16B 20/00; G16B 50/00; G16B 5/00; G16B 5/20; G16B 20/10; G16B 30/00; G16B 30/10; G16B 25/20; G16B 40/10; G16B 40/30; G16B 50/30; G16B 20/40; G16B 50/10; G06F 17/18
  See application file for complete search history.

(56) References Cited

U.S. PATENT DOCUMENTS

| | | | |
|---|---|---|---|
| 2014/0134650 A1 | 5/2014 | Hawtin et al. | |
| 2015/0174205 A1 | 6/2015 | Parker et al. | |
| 2016/0319361 A1* | 11/2016 | Spetzler | A61P 35/00 |
| 2018/0066262 A1* | 3/2018 | Domenyuk | C12Q 1/6886 |
| 2018/0171337 A1* | 6/2018 | O'Neill | A61K 47/6807 |
| 2018/0305689 A1* | 10/2018 | Sætrom | A61P 35/00 |
| 2019/0015331 A1* | 1/2019 | Elliman | A61P 3/00 |
| 2019/0276889 A1* | 9/2019 | Hecker | C12Q 1/6886 |
| 2020/0149012 A1* | 5/2020 | Elliman | C12N 5/0668 |

OTHER PUBLICATIONS

Ventetuolo et al. Biomarkers: diagnosis and Risk Assessment in Sepsis. Clinics in Chest Medicine. Dec. 2008 vol. 29 issue 4 pp. 591-603.*
James D. Faix (2013) Biomarkers of sepsis, Critical Reviews in Clinical Laboratory Sciences, 50:1, 23-36.*
Johnson S. et al. Gene expression profiles differentiate between sterile SIRS and early sepsis. Ann Surg. 2007 vol. 245 pp. 611-621.*
Kwan A. et al. Transcriptional instability during evolving sepsis may limit biomarker based risk stratification. Mar. 2013, PLOSONE vol. 8 No. 3 e60501.*
Maslove, D. et al. Gene expression profiling in sepsis: timing, tissue and translational considerations. 2014 Trends in Molecular Medicine, vol. 20 No. 4 pp. 204-213.*
Reinhart, K et al. New approaches to Sepsis: Molecular diagnostics and biomarkers. 2012, Clinical Microbiology Reviews, vol. 25 No. 4 pp. 609-634.*
Sweeney, T. et al. A comprehensive time-course-based multicohort analysis of sepsis and sterile inflammation reveals a robust diagnostic gene set. May 2015, Science Translational Medicine, vol. 7 issue 287, 287re71.*
Tang, B. et al. The use of Gene-expression profiling to identify candidate genes in human sepsis. 2007, Ann J Repair Crit. Care Med. vol. 176, pp. 676-684.*
Wong et al. Testing the prognostic accuracy of the updated pediatric sepsis biomarker risk model. 2014 PLOSONE vol. 9 issue 1 e86242.*
Bime, C. et al. Reactive oxygen species associated molecular signature predicts survival in patients with sepsis. 2016, Pulmonary Circulation, vol. 6 No. 2 p. 196-201.*
Salvo, I., et al., The Italian Sepsis study: preliminary results on the incidence and evolution of SIRS, sepsis, severe sepsis and septic shock. Intensive Care Med, 1995. 21 Suppl 2: p. S244-S249.
Levy, M.M., et al., 2001 SCCM/ESICM/ACCP/ATS/SIS International Sepsis Definitions Conference. Crit Care Med, 2003. 31(4): p. 1250-1256.
Victor, V.M., et al., Oxidative stress and mitochondrial dysfunction in sepsis: a potential therapy with mitochondria-targeted antioxidants. Infect Disord Drug Targets, 2009. 9(4): Abstract.
Galley, H.F., Oxidative stress and mitochondrial dysfunction in sepsis. Br J Anaesth, 2011. 107(1): p. 57-64.
Macdonald, J., H.F. Galley, and N.R. Webster, Oxidative stress and gene expression in sepsis. Br J Anaesth, 2003. 90(2): p. 221-232.
Quoilin, C., et al., Evidence of oxidative stress and mitochondrial respiratory chain dysfunction in an in vitro model of sepsis-induced kidney injury. Biochim Biophys Acta, 2014. 1837(10): p. 1790-1800.
Galley, H.F., Bench-to-bedside review: Targeting antioxidants to mitochondria in sepsis. Crit Care, 2010. 14(4): p. 230.
Zhang, Y. and N. Kaminski, Biomarkers in idiopathic pulmonary fibrosis. Curr Opin Pulm Med, 2012. 18(5): p. 441-446.
Selman, M., et al.. Gene expression profiles distinguish idiopathic pulmonary fibrosis from hypersensitivity pneumonitis. Am J Respir Crit Care Med, 2006. 173(2): p. 188-198.
Boon, K., et al., Molecular phenotypes distinguish patients with relatively stable from progressive idiopathic pulmonary fibrosis (IPF). PLoS One, 2009. 4(4): p. e5134.
Konishi, K., et al., Gene expression profiles of acute exacerbations of idiopathic pulmonary fibrosis. Am J Respir Crit Care Med, 2009. 180(2): p. 167-175.
Pandit, K.V., et al., Inhibition and role of let-7d in idiopathic pulmonary fibrosis. Am J Respir Crit Care Med, 2010. 182(2): p. 220-229.
Pandit, K.V., J. Milosevic, and N. Kaminski, MicroRNAs in idiopathic pulmonary fibrosis. Transl Res, 2011. 157(4): p. 191-199.
Navab, R., et al., Prognostic gene-expression signature of carcinoma-associated fibroblasts in non-small cell lung cancer. Proc Natl Acad Sci U S A, 2011. 108(17): p. 7160-7165.
Shedden, K., et al., Gene expression-based survival prediction in lung adenocarcinoma: a multi-site, blinded validation study. Nat Med, 2008. 14(8): p. 822-827.
Pitroda, S.P., et al., Tumor endothelial inflammation predicts clinical outcome in diverse human cancers. PLoS One, 2012. 7(10): p. e46104.
Herazo-Maya, J.D., et al., Peripheral blood mononuclear cell gene expression profiles predict poor outcome in idiopathic pulmonary fibrosis. Sci Transl Med, 2013. 5(205): p. 205ra136.
Desai, A.A., et al., A novel molecular signature for elevated tricuspid regurgitation velocity in sickle cell disease. Am J Respir Crit Care Med, 2012. 186(4): p. 359-368.
Kiliszek, M., et al., Altered gene expression pattern in peripheral blood mononuclear cells in patients with acute myocardial infarction. PLoS One, 2012. 7(11): p. e50054.
Zhou, T., et al., Peripheral blood gene expression as a novel genomic biomarker in complicated sarcoidosis. PLoS One, 2012. 7(9): p. e44818.
Zhou, T., T. Wang, and J.G. Garcia, A nonmuscle myosin light chain kinase-dependent gene signature in peripheral blood mononuclear cells is linked to human asthma severity and exacerbation status. Pulm Circ, 2015. 5(2): p. 335-338.
Zhou, T., T. Wang, and J.G. Garcia, Expression of nicotinamide phosphoribosyltransferase-influenced genes predicts recurrence-free survival in lung and breast cancers. Sci Rep, 2014. 4: p. 6107.

(56) References Cited

OTHER PUBLICATIONS

Zhou, T., T. Wang, and J.G. Garcia, Genes influenced by the non-muscle isoform of Myosin light chain kinase impact human cancer prognosis. PLoS One, 2014. 9(4): p. e94325.

Parnell, G.P., et al., Identifying key regulatory genes in the whole blood of septic patients to monitor underlying immune dysfunctions. Shock, 2013. 40(3): p. 166-174.

Tsalik, E.L., et al., An integrated transcriptome and expressed variant analysis of sepsis survival and death. Genome Med, 2014. 6(11): p. 111.

Kanehisa, M., et al., The KEGG resource for deciphering the genome. Nucleic Acids Res, 2004. 32(Database issue): p. D277-D280.

Huang da, W., B.T. Sherman, and R.A. Lempicki, Systematic and integrative analysis of large gene lists using DAVID bioinformatics resources. Nat Protoc, 2009. 4(1): p. 44-57.

Dennis, G., Jr., et al., DAVID: Database for Annotation, Visualization, and Integrated Discovery. Genome Biol, 2003. 4(5): p. P3.

Ashburner, M., et al., Gene ontology: tool for the unification of biology. The Gene Ontology Consortium. Nat Genet, 2000. 25(1): p. 25-29.

\* cited by examiner

Hypergeometric P = 0.012

US 11,230,735 B2

SYSTEMS AND METHODS FOR CHARACTERIZING SEPSIS

CROSS-REFERENCE TO RELATED APPLICATIONS

This application is a Section 371 U.S. national stage entry of International Patent Application No. PCT/US2016/068487, International Filing Date Dec. 23, 2016 which claims priority to and the benefit of U.S. Provisional Application No. 62/387,580, filed Dec. 24, 2015, which are hereby incorporated by reference in their entireties.

STATEMENT REGARDING GOVERNMENT FUNDING

This invention was made with government support under Grant No. R01 HL091899 awarded by NIH and Grant No. IK2BX001477 awarded by VA. The government has certain rights in the invention.

FIELD OF THE INVENTION

The present disclosure relates to methods of characterizing disease. In particular, this invention relates to methods for selecting a treatment, treating, and predicting survival time in subjects suffering from sepsis, based on the characterization of genes associated with a reactive oxygen species (ROS) molecular signature.

BACKGROUND OF THE INVENTION

Sepsis-related multiple organ dysfunction syndrome is a leading cause of death in intensive care units (ICUs). There is overwhelming evidence that oxidative stress plays a significant role in the pathogenesis of sepsis-associated multiple organ failure; however reactive oxygen species (ROS)-associated biomarkers and/or diagnostics which define mortality or predict survival are lacking. New biomarkers for predicting survival and its potential for facilitating individualized therapies for sepsis are needed.

SUMMARY OF THE INVENTION

Experiments conducted during the course of developing embodiments for the present invention identified ROS-associated biomarkers predictive of survival in septic patients. In silico analyses of expression profiles allowed the identification of a 21 gene ROS-associated molecular signature that predicts survival in septic patients. Importantly, this signature performed well in a validation cohort comprised of septic patients aggregated from distinct patient populations recruited from different sites. The signature outperformed randomly generated signatures with the same gene size. The findings further validate the critical role of ROS in the pathogenesis of sepsis and provide a novel gene signature that predicts survival in septic patients. These results also highlight the utility of peripheral blood molecular signatures as biomarkers for predicting mortality risk in septic patients, which could facilitate the development of personalized therapies.

Accordingly, the present disclosure relates to methods of characterizing disease. In particular, this invention relates to methods for selecting a treatment, treating, and predicting survival time in subjects suffering from sepsis, based on the characterization of genes associated with a reactive oxygen species (ROS) molecular signature.

For example, in certain embodiments, the present invention provides methods of predicting survival time for a human subject suffering from sepsis, the method comprising obtaining a biological sample from the subject; determining gene expression levels of CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, or KEAP1 in the biological sample; comparing the gene expression levels to reference gene expression levels, wherein the reference gene expression levels are gene expression levels of CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, or KEAP1 for one or more of subjects not having sepsis and subjects having non-life threatening sepsis; and predicting longer survival time if gene expression levels are consistent with reference gene expression levels, or predicting shorter survival time if gene expression levels are inconsistent with the reference gene expression levels. In some embodiments, the biological sample comprises peripheral blood mononuclear cells. In some embodiments, the methods further comprise communicating the predicted survival time to the subject or a health care provider.

In certain embodiments, the present invention provides methods of monitoring the treatment of sepsis in a human subject, the method comprising obtaining a biological sample from a subject being treated for sepsis; determining gene expression levels of CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, or KEAP1 in the biological sample; comparing the gene expression levels to reference gene expression levels, wherein the reference gene expression levels are gene expression levels of CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, or KEAP1 for one or more of subjects not having sepsis and subjects having non-life threatening sepsis; identifying the treatment as a favorable treatment response if gene expression levels are consistent with reference gene expression levels, or identifying the treatment as an unfavorable treatment response if gene expression levels are inconsistent with the reference gene expression levels. In some embodiments, the biological sample comprises peripheral blood mononuclear cells. In some embodiments, the methods further comprise communicating the effectiveness of the treatment to the subject or a health care provider.

In certain embodiments, the present invention provides a method of characterizing sepsis, comprising: a) assaying a sample from a subject exhibiting at least one symptom of sepsis for the presence of altered expression of one or more genes selected from, for example, CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, or KEAP1; and b) characterizing sepsis in the subject based on the presence of said altered gene expression. In some embodiments, expression of the genes relative to the level in a subject not diagnosed with sepsis is indicative of increased risk of death from sepsis. In some embodiments, the method further comprises the step of calculating a risk score for the subject. In some embodiments, the risk score comprises a linear combination of expression values of the genes. In some embodiments, the risk score is calculated using the formula:

$$S = \sum_{i=1}^{n} W_i(e_i - \mu_i)/\tau_i,$$

where S is the risk score of the patient; n is the number of genes in the iCG signature; $W_i$ denotes the weight of gene i as shown in Table 2; $e_i$ denotes the expression level of gene i; and $\mu_i$ and $\tau_i$ are the mean and standard deviation of the gene expression values for gene i across all samples, respectively. In some embodiments, a higher positive number score of said risk score is indicative of the subject having or being at risk of death from sepsis. In some embodiments, the at least one gene is at least 2 (e.g., at least 5, 10, 15, 20 or all) of the genes. In some embodiments, the sample is whole blood, plasma, serum, or urine. In some embodiments, the detecting comprises forming a complex between the genes and a nucleic acid primer, probe, or pair of primers that specifically bind to the genes. In some embodiments, the genes are associated with reactive oxygen species.

Further embodiments provide at least two complexes comprising a nucleic acid encoding a gene selected from two or more (e.g., 5, 10, 15, 20, or all) genes selected from the group consisting of one or more genes selected from, for example, CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, or KEAP1; and at least two distinct nucleic acid primers or probes that specifically hybridize to the two or more genes.

Additional embodiments provide a kit, comprising: reagents for detecting altered expression levels of two or more (e.g., 5, 10, 15, 20, or all) genes selected from, for example, CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, or KEAP1, DNAJB6, and KEAP1. In some embodiments, the reagents are at least two nucleic acid primers or probes that specifically hybridizes to the two or more genes. In some embodiments, the nucleic acid primers or probes are at least 8, 10, or 20 nucleic acids in length.

Yet other embodiments provide a system, comprising: a) a computer processor; and b) computer software configured to analyze information on the presence of altered expression of two or more (e.g., 5, 10, 15, 20, or all) genes selected from, for example, CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, or KEAP1; and determine a risk of dying of sepsis in a subject based on the presence of the altered levels of expression of the genes.

Still further embodiments provide a method of characterizing gene expression, comprising: a) assaying a sample from a subject exhibiting at least one symptom of sepsis for the presence of altered expression of two or more genes (e.g., 5, 10, 15, 20, or all) selected from, for example, CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, or KEAP1.

Additional embodiments are described herein.

DESCRIPTION OF THE FIGURES

The patent or application file contains at least one drawing executed in color. Copies of this patent or patent application publication with color drawing(s) will be provided by the Office upon request and payment of the necessary fee.

DEFINITIONS

Figure 1:
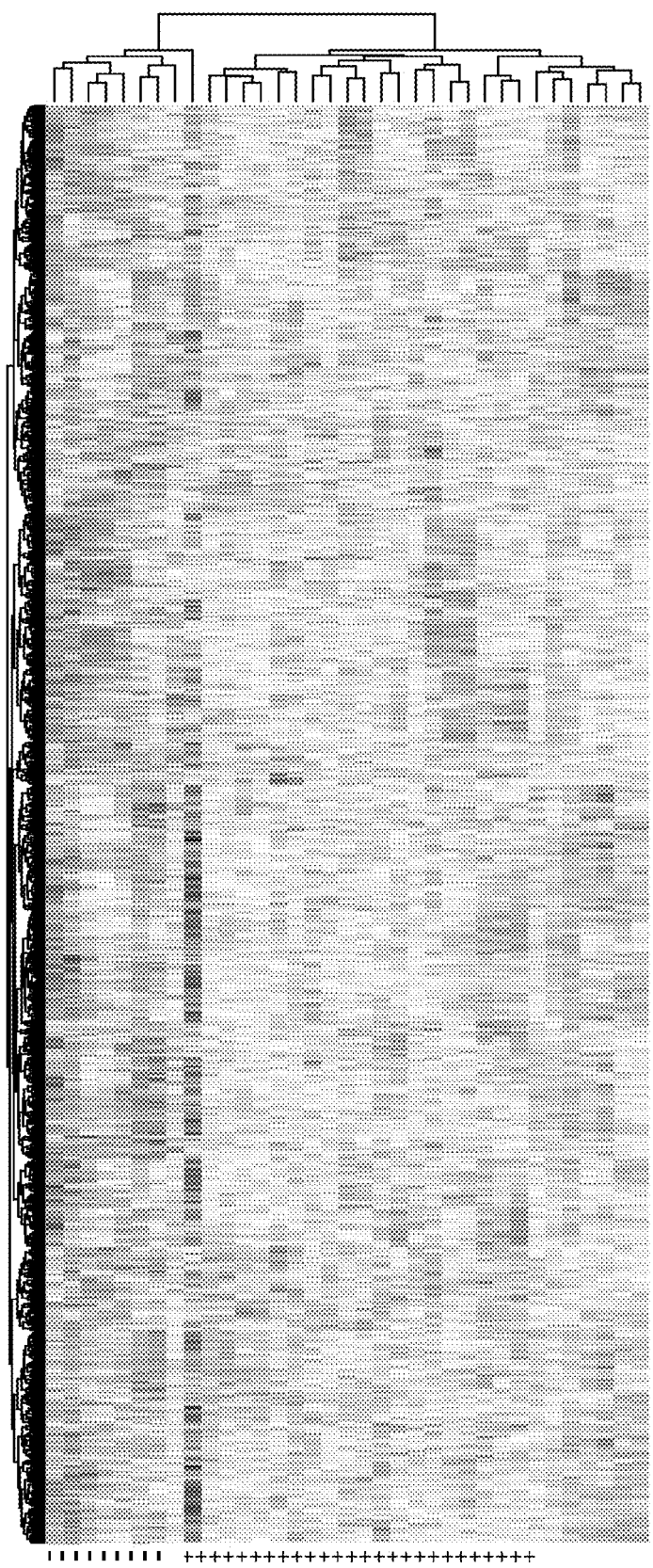
FIG. 1. Differentially expressed genes associated with survival and non-survival in septic patients. The heatmap is generated based on the PBMC gene expression; red represents increased expression while blue represents decreased expression.

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "subject" refers to any organisms that are screened using the diagnostic methods described herein. Such organisms preferably include, but are not limited to, mammals (e.g., humans).

The term "diagnosed," as used herein, refers to the recognition of a disease by its signs and symptoms, or genetic analysis, pathological analysis, histological analysis, and the like.

"Fibrosis" means the formation or development of excess fibrous connective tissue in an organ or tissue. In certain embodiments, fibrosis occurs as a reparative or reactive process. In certain embodiments, fibrosis occurs in response to damage or injury. The term "fibrosis" is to be understood as the formation or development of excess fibrous connective tissue in an organ or tissue as a reparative or reactiv As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragments are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues (e.g., biopsy samples), cells, and gases. Biological samples include blood products, such as plasma, serum and the like. Such examples are not however to be construed as limiting the sample types applicable to the present invention.

DETAILED DESCRIPTION OF THE INVENTION

Sepsis syndrome is one of the leading causes of morbidity and mortality amongst critically ill patients in ICUs. The sepsis syndrome manifests as a spectrum of conditions including; systemic inflammatory response syndrome (SIRS), sepsis, severe sepsis, septic shock and multiple organ system dysfunction. The overall mortality rate ranges from 26% in patients with SIRS to 82% in patients with septic shock [1, 2]. Unfortunately, there are currently no available diagnostic biomarkers predictive of survival in patients with sepsis. Traditional biomarkers such as C-reactive protein, interleukin-6, or procalcitonin do not predict survival. Interestingly, there is overwhelming evidence implicating an underlying role of oxidative stress in the pathogenesis of sepsis [3-6]. Under normal physiologic conditions, redox balance exists through a complex interplay of genes which mediate oxidant generation and antioxidant capacity. An imbalance between the production of reactive oxygen species (ROS) and the detoxification of their reactive intermediates results in oxidative stress. Numerous studies demonstrate an association between sepsis and elevated oxidative stress levels [4, 6, 7]. It is likely that sepsis triggers the alteration of the activity of various genes that mediate both oxidant generation and/or antioxidant capacity.

Over the past two decades, there have been major advances in our understanding of the underlying biologic features of sepsis. However, these findings have not been successfully translated to effective therapies. One potential barrier to the development of effective therapies and improved survival outcomes is the paucity of reliable biomarkers for diagnosis, prognosis, and responses to therapy. Biomarker studies are often limited by the number of candidate biomarkers, cohort size, and lack of replication using a validation cohort [8]. Technological advancements have enabled the utility of expression microarrays providing analysis of genome-level profiles capable of generating molecular signatures, either from disease tissues [9-16] or peripheral mononuclear cells (PBMCs) [17-19]. We have previously employed this strategy to identify diagnostic and/or prognostic biomarkers for several respiratory diseases such as sarcoidosis [20], idiopathic pulmonary fibrosis [17], asthma [21], and lung cancers [22, 23].

Experiments conducted during the course of developing embodiments for the present invention analyzed previously generated microarray gene expression data from peripheral blood mononuclear cells (PBMCs) of septic patients, and constructed the first ROS genes expression-based signature capable of predicting the odds of patients' outcome. In silico analyses of expression profiles and phenotypic data allowed the generation of a 21-gene ROS-associated molecular signature that predicts survival, in both the discovery and validation cohorts. These results demonstrate the feasibility of using peripheral blood to identify molecular signatures which can serve as novel biomarkers for predicting survival and its potential for facilitating individualized therapies.

I. Diagnostic and Screening Methods

As described above, embodiments of the present invention provide diagnostic and screening methods that utilize the detection of altered gene expression levels of one or more genes (e.g., 1, 2, 3, 4, 5, 6, 7, 8, 9, 10, 11, 12, 13, 14, 15, 16, 17, 18, 19, 20, or all) of CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, and KEAP1

Exemplary, non-limiting methods are described below.

In some embodiments, altered expression of one or more of the genes described herein are indicative of a diagnosis, characterization, or increased risk of death from sepsis.

Any patient sample suspected of containing the genes may be tested according to methods of embodiments of the present invention. By way of non-limiting examples, the sample may be blood, urine, or a fraction thereof (e.g., plasma, serum, cells).

In some embodiments, the patient sample is subjected to preliminary processing designed to isolate or enrich the sample for the genes or cells that contain the gene. A variety of techniques known to those of ordinary skill in the art may be used for this purpose, including but not limited to: centrifugation; immunocapture; cell lysis; and, nucleic acid target capture (See, e.g., EP Pat. No. 1 409 727, herein incorporated by reference in its entirety).

In some embodiments, expression levels of the genes are detected along with other markers in a multiplex or panel format. Markers are selected for their predictive value alone or in combination with the levels of genes expression. Markers for other diseases, infections, and metabolic conditions are also contemplated for inclusion in a multiplex or panel format.

i. DNA and RNA Detection

The levels of gene expression of the genes described herein are detected using a variety of nucleic acid techniques known to those of ordinary skill in the art, including but not limited to: nucleic acid sequencing; nucleic acid hybridization; and, nucleic acid amplification.

1. Sequencing

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing (see, e.g., Astier et al., J. Am. Chem. Soc. 2006 Feb. 8; 128(5):1705-10, herein incorporated by reference) is utilized. The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences (Voelkerding et al., *Clinical Chem.*, 55: 641-658, 2009; MacLean et al., *Nature Rev. Microbiol.*, 7: 287-296; U.S. Pat. Nos. 7,169,560; 7,282,337; 7,482,120; 7,501,245; 6,818,395; 6,911,345; 7,501,245; each herein incorporated by reference in their entirety) is utilized. Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

Stratos Genomics, Inc. sequencing involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

2. Hybridization

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, altered gene expression is detected using fluorescence in situ hybridization (FISH). In some embodiments, FISH assays utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present invention further provides a method of performing a FISH assay on human cells (e.g., breast or endometrial cells). Specific protocols are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). There are also kits that are commercially available and that provide protocols for performing FISH assays (available from e.g., Oncor, Inc., Gaithersburg, MD). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

3. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., those described in table 1) by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

4. Amplification

Nucleic acids may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

5. Protein Detection

In some embodiments, altered levels gene expression are detected by detected altered levels of polypeptides encoded by the genes (e.g., using immunoassays or mass spectrometry).

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays. Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

Mass spectrometry has proven to be a valuable tool for the determination of molecular structures of molecules of many kinds, including biomolecules, and is widely practiced today. Purified proteins are digested with specific proteases (e.g. trypsin) and evaluated using mass spectrometry. Many alternative methods can also be used. For instance, either matrix-assisted laser desorption/ionization (MALDI) or electrospray ionization (ESI) mass spectrometric methods can be used. Furthermore, mass spectroscopy can be coupled with the use of two-dimensional gel electrophoretic separation of cellular proteins as an alternative to comprehensive pre-purification. Mass spectrometry can also be coupled with the use of peptide fingerprint database and various searching algorithms. Differences in post-translational modification, such as phosphorylation or glycosylation, can also be probed by coupling mass spectrometry with the use of various pretreatments such as with glycosylases and phosphatases. All of these methods are to be considered as part of this application.

In some embodiments, electrospray ionisation quadrupole mass spectrometry is utilized to detect polypeptide levels (See e.g., U.S. Pat. No. 8,658,396; herein incorporated by reference in its entirety).

6. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., gene expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of altered levels of gene expression of the genes in Tables 1 or 2) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

6. Compositions & Kits

Compositions for use in the diagnostic methods described herein include, but are not limited to, probes, amplification oligonucleotides, and the like. In some embodiments, kits include all components necessary, sufficient or useful for detecting the markers described herein (e.g., reagents, controls, instructions, etc.). The kits described herein find use in research, therapeutic, screening, and clinical applications.

The probe and antibody compositions of the present invention may also be provided in the form of an array.

In some embodiments, the present invention provides one or more nucleic acid probes or primers having 8 or more (e.g., 10 or more, 12 or more, 15 or more, 18 or more, etc.) nucleotides, and that specifically bind to nucleic acids encoding one or more of the genes in table 2. In some embodiments, the present invention provides an antibody that specifically binds to one or more of the genes in table 2.

Embodiments of the present invention provide complexes of two or more nucleic acids or polypeptides described in table 1 with nucleic acid primers or probes or antibodies. In some embodiments, the present invention provides a multiplex (e.g., microarray) comprising reagents that binds to two or more nucleic acids or polypeptides described in tables 1 or 2.

Experimental

The following examples are provided in order to demonstrate and further illustrate certain preferred embodiments and aspects of the present invention and are not to be construed as limiting the scope thereof.

EXAMPLE 1

Methods

Subjects and Blood Samples

For the discovery cohort (GEO accession: GSE54514), whole-blood samples were collected from a total of 35 subjects with confirmed sepsis at day 1 of ICU [24]. The diagnosis of sepsis was based on documented bacterial infection, meeting SIRS criteria, and consensus by the consulting physician that sepsis was the cause of the patients ICU stay [14]. The validation cohort (GEO accession: GSE63042 #) [25] included patients who met at least two SIRS criteria plus a suspected or known acute infection [15]. Peripheral blood samples were collected from 106 patients. We segregated the septic patients into two groups: survivors and non-survivors. Specifically, we utilized data from 35 patients (9 non-survivors and 26 survivors) as the discovery cohort and data from 106 patients (28 non-survivors and 78 survivors) as the validation cohort. For the samples in the discovery cohort, whole-genome gene expression pattern was profiled by Illumina HumanHT-12 V3.0 expression beadchip while the gene expression data in the validation cohort were obtained by high-throughput sequencing using Illumina Genome Analyzer II. The study was approved by the Institutional Review Boards of each institution with written informed consent obtained from the patient or their relatives [24, 25].

Risk Score

A risk score was calculated for each patient using a linear combination of expression values of genes in the iCG signature [16, 22, 23]. The formula is shown below:

$$S = \sum_{i=1}^{n} W_i(e_i - \mu_i)/\tau_i$$

Here, S is the risk score of the patient; n is the number of genes in the iCG signature; $W_i$ denotes the weight of gene i (as shown in Table 2), which indicates the direction of deregulation for gene i (1 or −1); $e_i$ denotes the expression level of gene i; and $\mu_i$ and $\tau_i$ are the mean and standard deviation of the gene expression values for gene i across all samples, respectively.

Results

Patient Characteristics

Our in silico study focused on 35 patients (9 non-survivors and 26 survivors) as the discovery cohort and 106 patients (28 non-survivors and 78 survivors) as the validation cohort. The characteristics of individuals included in our analyses for survivors and non-survivors within the discovery and validation cohorts are presented (Table 1).

Identifying Differentially Expressed Genes in Blood Associated with Survival of Septic Patients To determine differentially-expressed protein-coding genes in PBMCs associated with survival of septic patients, we first analyzed gene expression patterns in the discovery cohort. We then linked gene expression levels with survival. We identified 450 up-regulated genes and 1027 down-regulated genes in non-survivors compared to survivors (FIG. 1).

Figure 2:
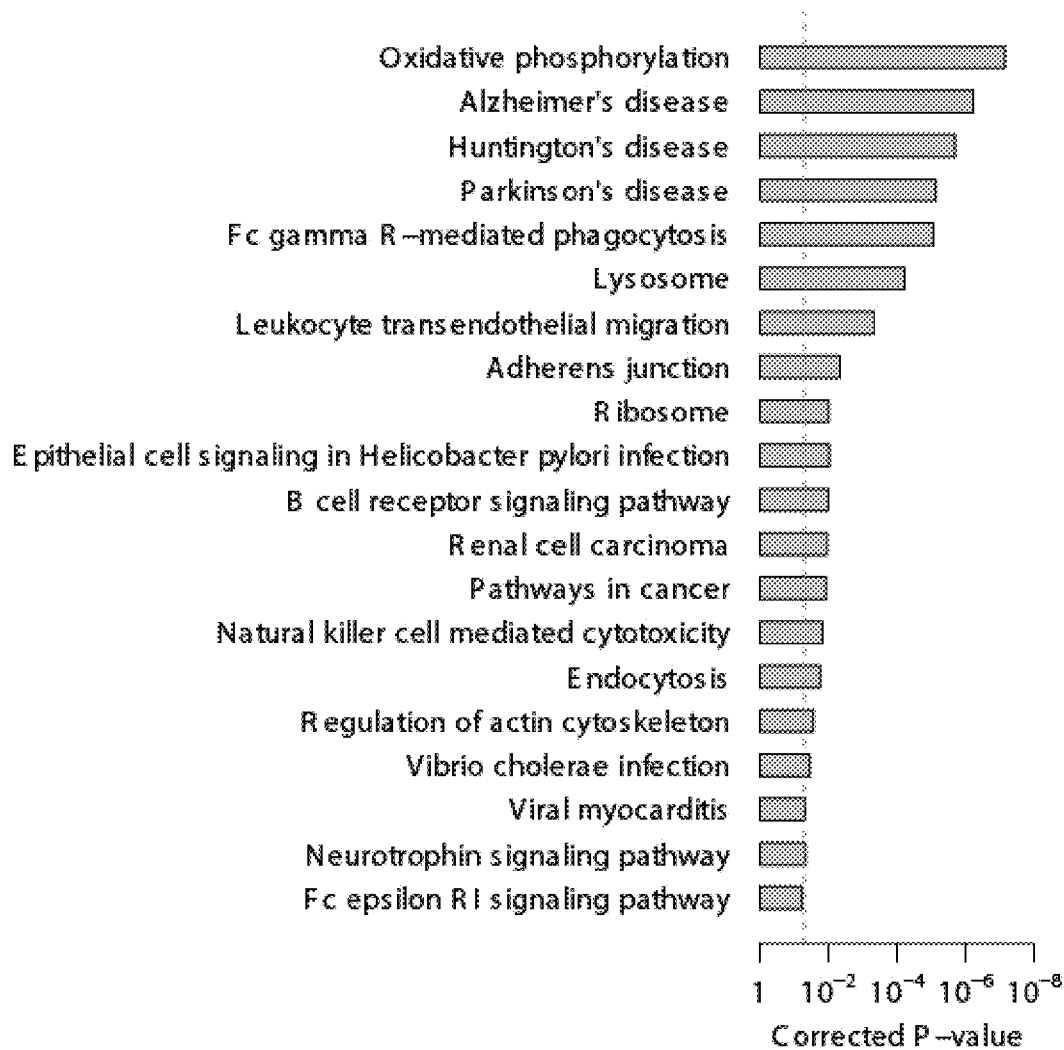
FIG. 2. Enriched pathways among the differentially expressed genes between survivor and non-survivor septic patients. The top 20 ranked KEGG pathways are listed. The dotted line indicates the cutoff of significance (0.05). Fisher's exact test was used to calculate the P-values.
Figure 3:
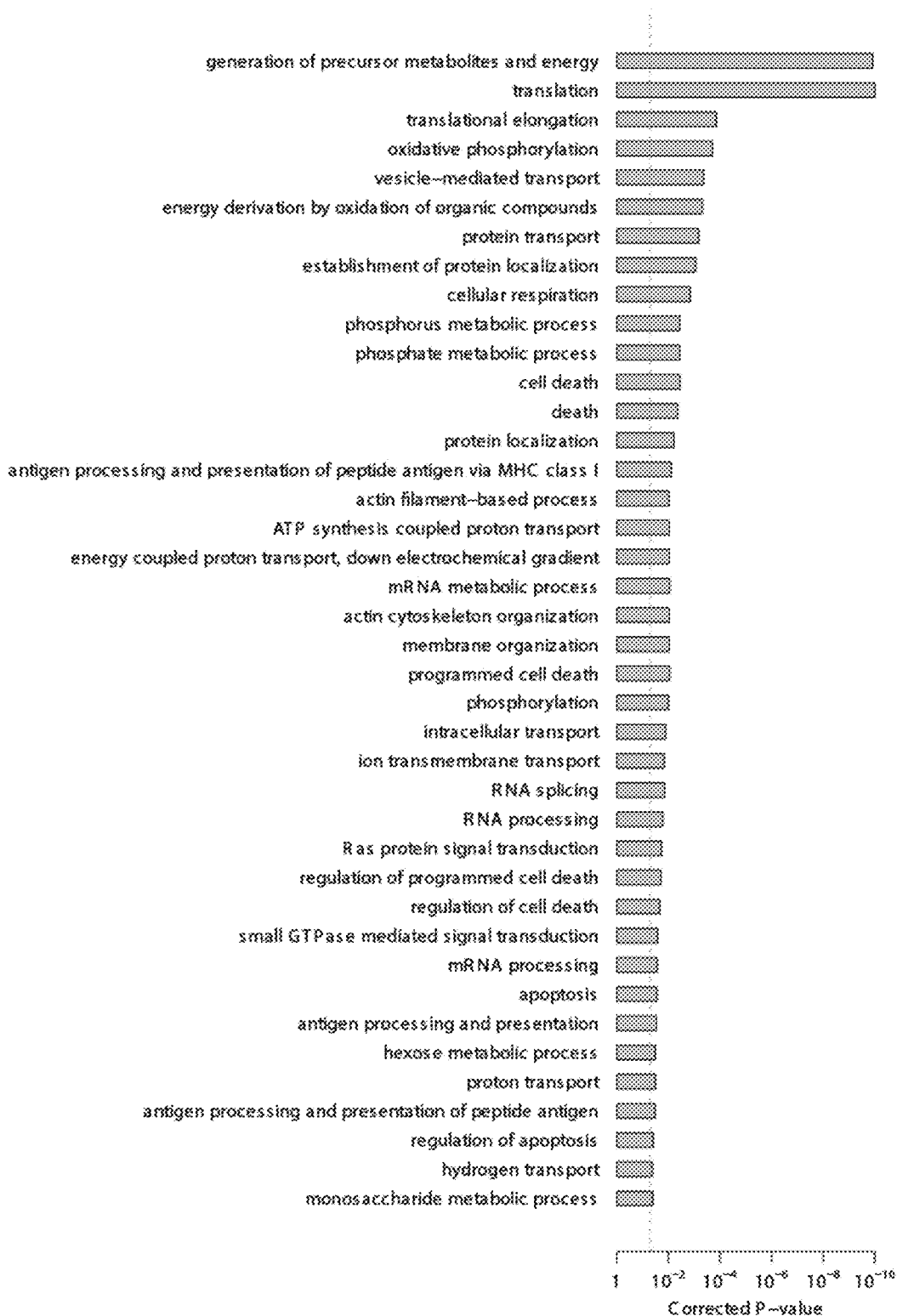
FIG. 3. The top 40 GO biological process terms associated with the differentially expressed genes between survivors and non-survivors. The dotted line indicates the cutoff of significance (0.05). Fisher's exact test was used to calculate the P-values.

We searched for any enriched Kyoto Encyclopedia of Genes and Genomes (KEGG) [26] physiological pathways among the differentially expressed genes using the NIH/DAVID [27, 28]. Our analyses revealed 19 KEGG pathways associated with differentially expressed genes (P<0.05); top KEGG pathways significantly associated with differentially expressed genes were identified, with "Oxidative phosphorylation" as the most significantly altered KEGG pathway (FIG. 2. Gene ontology analysis on GO biological process terms [29] also confirmed that oxidative phosphorylation is significantly associated with the differentially expressed gene between survivors and non-survivors (FIG. 3).

In Silico Analysis of ROS-Associated Genes

Figure 4A:
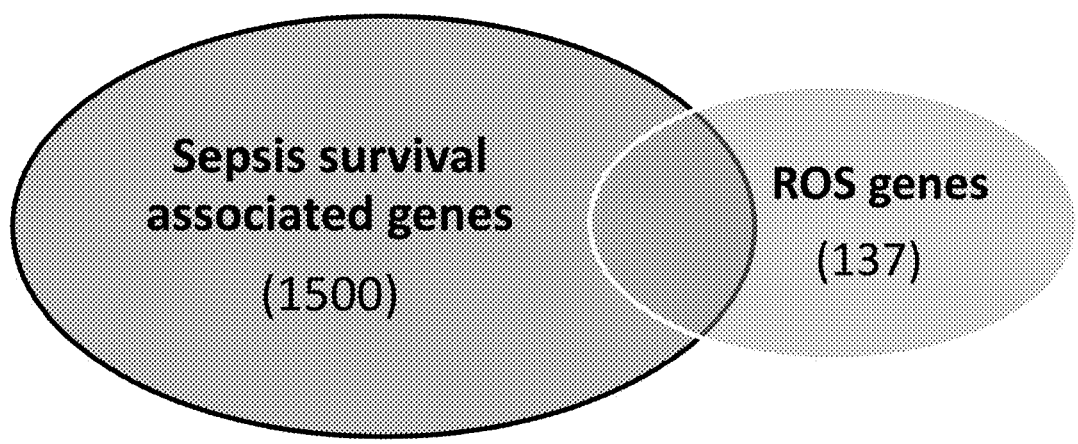
FIG. 4. ROS-associated gene signature in septic patients. (A) Schematic diagram representing genome-wide and ROS-associated overlapping genes. Twenty-one overlapped genes were identified, which is statistically significant (hypergeometic test: P=0.012). (B) Heatmap representing the 21 differentially expressed ROS-associated genes. Red represents increased gene expression while blue represents decreased expression. Patients are characterized as survivor (+) and non-survivor (−).
Figure 4B:
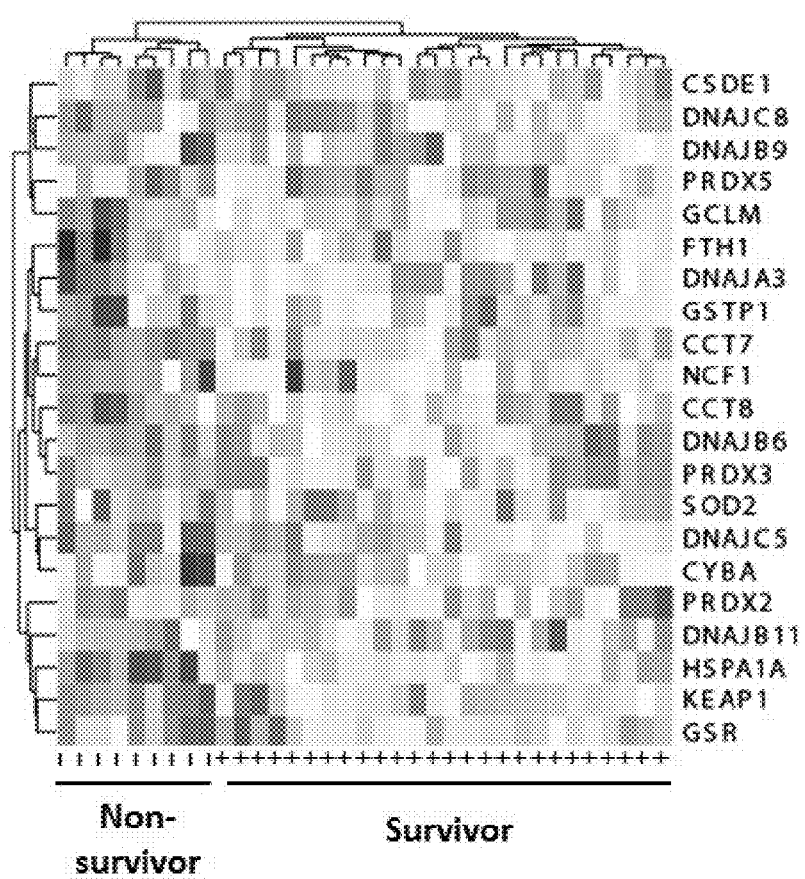

We identified a group of 137 genes that are known to play a role in mediating reactive oxygen species (ROS) levels (Table 2). This list includes genes involved in oxidant generation (such as NADPH-oxidases), metabolism (superoxide dismutases), and/or antioxidant response genes (Nrf2 glutathione peroxidases, peroxiredoxins). Interestingly, we confirmed that these deregulated genes are significantly enriched in sepsis survival related genes (cumulative hypergeometric test: P=0.012), suggesting a statistical significant overlap (21 genes) between ROS genes and sepsis survival related genes (FIG. 4A). We designated the genes within the overlap as a 21-gene signature (Table 3 and FIG. 4B). The weights listed in Table 3 indicate the direction of differential gene expression in non-survivors.

21-Gene Signature Associated with Survival in the Discovery Cohort

Figure 5A:
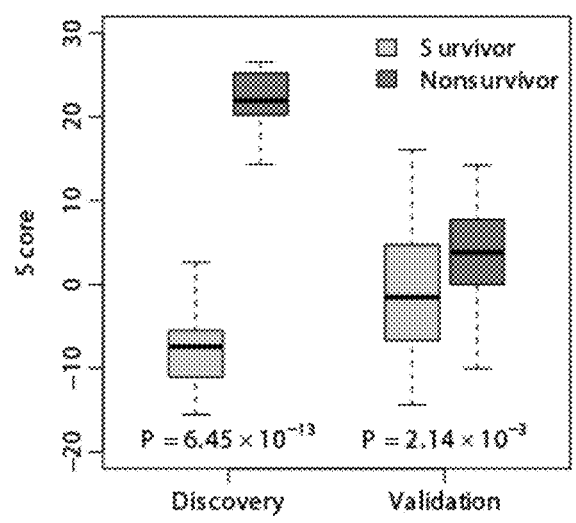
FIG. 5. The 21-gene signature based risk score. (A) The 21-gene signature based risk score differentiates the non-survivors from the survivors in both the discovery and validation cohorts. The boxplot indicates the distribution of the risk score in each category. (B) The ROC curves of the 21-gene signature in distinguishing non-survivors from survivors in both the discovery and validation cohorts. (C) Superior predictive power of the 21-gene based risk score compared with random gene signature. The grey area shows the AUC for 1,000 resampled gene signatures picked up from human genome with identical size as the 21-gene signature. The black triangle stands for the AUC value of our 21-gene signature. Right-tailed P-value of the sampling distribution was calculated.
Figure 5B:
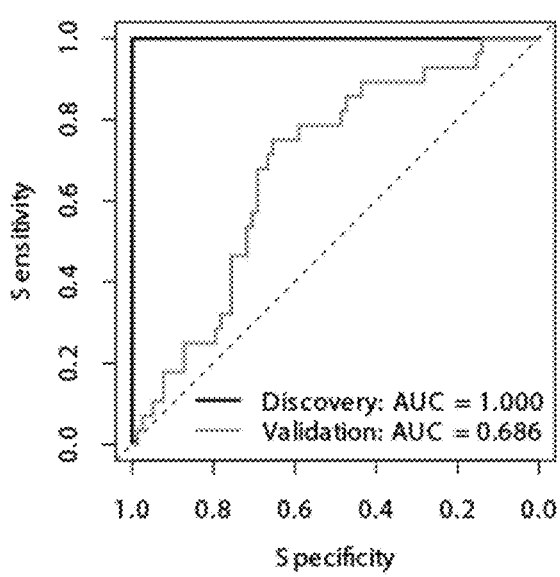

Based on the 21-gene signature, we constructed a scoring system to assign each subject a risk score, representing a linear combination of the 21-gene expression values, weighted by the direction of differential expression: 1 for the up-regulated and −1 for the down-regulated genes in non-survivor (see Methods for details). A higher risk score suggests a poorer clinical outcome. Our in silico analyses focused on 35 patients (9 non-survivors and 26 survivors) as the discovery cohort (Table 1). As expected, the risk score of non-survivors were significantly higher than that of survivors in the discovery cohort (t-test: $P=6.45\times10^{-13}$) (FIG. 5A). The area under the receiver operating characteristic (ROC) curve (AUC) were 1.000 (FIG. 5B).

Validating the 21 ROS-Associated Gene Signature

We utilized a second dataset as validation cohort (Table 1), where a unique risk score was assigned to each patient based on the expression of the 21-gene signature. Interestingly, our signature performs well in predicting the patients' survival. The 21-gene based risk score of non-survivors were significantly higher than that of survivors in the validation cohort (t-test: $P=2.14\times10^{-3}$) (FIG. 5A). The AUC were 0.686 (FIG. 5B).

Figure 5C:
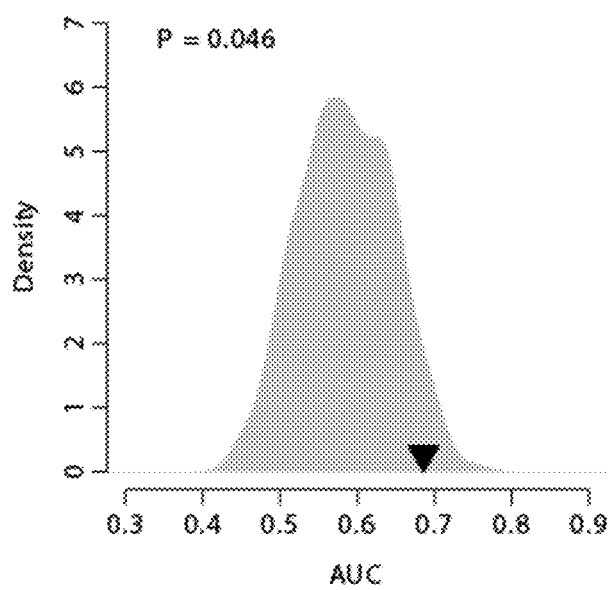

We also conducted a resampling test to confirm the predictive power of the 21-gene signature. We obtained 1,000 random gene signatures by randomly selecting 21 genes from human genome and calculated the AUC for each random gene signature. It is of interest that relative to randomly generated signatures composed of the same number of genes, our signature outperforms significantly better (right-tailed: P=0.046), highlighting a truly existing biological signal (FIG. 5C).

TABLE 1

Characteristics of individuals included in analyses.

| | Discovery Cohort [GEO accession #] | | Validation Cohort [GEO accession #] | |
|---|---|---|---|---|
| | Survivors | Non-Survivors | Survivors | Non-Survivors |
| Number in group | 26 | 9 | 78 | 28 |
| Age (years) | 57 ± 18 | 70 ± 11 | 56.1 ± 18 | 67.6 ± 17 |
| Gender (% male) | 38% | 44% | 59% | 61% |
| APACHE II | 19 ± 6 | 24 ± 5 | 14.7 ± 6.6 | 21.3 ± 7.1 |

Data are presented as mean ± SD

TABLE 2

| ROS Genes | |
|---|---|
| ALB | albumin |
| ALOX12 | arachidonate 12-lipoxygenase |
| APOE | apolipoprotein E |
| ATOX1 | ATX1 antioxidant protein 1 homolog |
| BAG1 | BCL2-associated athanogene |
| BCL2 | B-cell CLL/lymphoma 2 |
| BNIP3 | BCL2/adenovirus E1B 19 kDa interacting protein 3 |
| CALR | calreticulin |
| CANX | calnexin |
| CAT | catalase |
| CCL5 | chemokine (C-C motif) ligand 5 |
| CCS | copper chaperone for superoxide dismutase |
| CCT2 | chaperonin containing TCP1, subunit 2 (beta) |
| CCT3 | chaperonin containing TCP1, subunit 3 (gamma) |
| CCT4 | chaperonin containing TCP1, subunit 4 (delta) |
| CCT5 | chaperonin containing TCP1, subunit 5 (epsilon) |
| CCT7 | chaperonin containing TCP1, subunit 7 (eta) |
| CCT8 | chaperonin containing TCP1, subunit 8 (theta) |
| CES1 | carboxylesterase 1 (monocyte/macrophage serine esterase 1) |
| CSDE1 | cold shock domain containing E1, RNA-binding |
| CYBA | cytochrome b-245, alpha polypeptide |
| CYBB | cytochrome b-245, beta polypeptide (chronic granulomatous disease) |
| CYP11A1 | cytochrome P450, family 11, subfamily A, polypeptide 1 |

TABLE 2-continued

ROS Genes

| | |
|---|---|
| CYP11B2 | cytochrome P450, family 11, subfamily B, polypeptide 2 |
| CYP1A1 | cytochrome P450, family 1, subfamily A, polypeptide 1 |
| CYP1B1 | cytochrome P450, family 1, subfamily B, polypeptide 1 |
| CYP2C19 | cytochrome P450, family 2, subfamily C, polypeptide 19 |
| CYP2D6 | cytochrome P450, family 2, subfamily D, polypeptide 6 |
| CYP2F1 | cytochrome P450, family 2, subfamily F, polypeptide 1 |
| DHCR24 | 24-dehydrocholesterol reductase |
| DNAJA1 | DnaJ (Hsp40) homolog, subfamily A, member 1 |
| DNAJA2 | DnaJ (Hsp40) homolog, subfamily A, member 2 |
| DNAJA3 | DnaJ (Hsp40) homolog, subfamily A, member 3 |
| DNAJA4 | DnaJ (Hsp40) homolog, subfamily A, member 4 |
| DNAJB1 | DnaJ (Hsp40) homolog, subfamily B, member 1 |
| DNAJB11 | DnaJ (Hsp40) homolog, subfamily B, member 11 |
| DNAJB12 | DnaJ (Hsp40) homolog, subfamily B, member 12 |
| DNAJB2 | DnaJ (Hso40) homolog, subfamily B, member 2 |
| DNAJB4 | DnaJ (Hsp40) homolog, subfamily B, member 4 |
| DNAJB5 | DnaJ (Hsp40) homolog, subfamily B, member 5 |
| DNAJB6 | DnaJ (Hsp40) homolog, subfamily B, member 6 |
| DNAJB9 | DnaJ (Hsp40) homolog, subfamily B, member 9 |
| DNAJC1 | DnaJ (Hsp40) homolog, subfamily C, member 1 |
| DNAJC4 | DnaJ (Hsp40) homolog, subfamily C, member 4 |
| DNAJC5 | DnaJ (Hsp40) homolog, subfamily C, member 5 |
| DNAJC7 | DnaJ (Hsp40) homolog, subfamily C, member 7 |
| DNAJC8 | DnaJ (Hsp40) homolog, subfamily C, member 8 |
| DNAJC9 | DnaJ (Hsp40) homolog, subfamily C, member 9 |
| DUOX1 | dual oxidase 1 |
| DUSP1 | dual specificity phosphatase 1 |
| EPHX2 | epoxide hydrolase 2 |
| EPX | eosinophil peroxidase |
| FMO4 | flavin containing monooxygenase 4 |
| FMO5 | flavin containing monooxygenase 5 |
| FOS | v-fos FBJ murine osteosarcoma viral oncogene homolog |
| FOXM1 | forkhead box M1 |
| FTH1 | ferritin, heavy polypeptide 1 |
| GCLC | glutamate-cysteine ligase, catalytic subunit |
| GCLM | glutamate-cysteine ligase, modifier subunit |
| GLRX2 | glutaredoxin 2 |
| GPR156 | G protein-coupled receptor 156 |
| GPX1 | glutathione peroxidase 1 |
| GPX3 | glutathione peroxidase 3 |
| GPX4 | glutathione peroxidase 4 |
| GPX6 | glutathione peroxidase 6 |
| GPX7 | glutathione peroxidase 7 |
| GSR | glutathione reductase |
| GSS | glutathione synthetase |
| GSTA5 | glutathione S-transferase A5 |
| GSTP1 | glutathione S-transferase pi |
| GSTZ1 | glutathione transferase zeta 1 |
| GTF2I | general transcription factor II, i |
| HIF1A | hypoxia-inducible factor 1, alpha subunit |
| HIP2 | huntingtin interacting protein 2 |
| HMOX1 | heme oxygenase (decycling) 1 |
| HMOX2 | heme oxygenase (decycling) 2 |
| HOPX | HOP homeobox |
| HSPA1A | heat shock 70 kDa protein 1A |
| HSPA1L | heat shock 70 kDa protein 1-like |
| HSPA2 | heat shock 70 kDa protein 2 |
| HSPA4 | heat shock 70 kDa protein 4 |
| HSPA5 | heat shock 70 kDa protein 5 |
| HSPA8 | heat shock 70 kDa protein 8 |
| HSPA9 | heat shock 70 kDa protein 9 |
| HSPB1 | heat shock 27 kDa protein 1 |
| HSPB2 | heat shock 27 kDa protein 2 |
| HSPD1 | heat shock 60 kDa protein 1 |
| HSPE1 | heat shock 10 kDa protein 1 |
| JUNB | jun B proto-oncogene |
| KEAP1 | kelch-like ECH-associated protein 1 |
| KRT1 | keratin 1 |
| MB | myoglobin |
| MGST3 | microsomal glutathione S-transferase 3 |
| MPO | myeloperoxidase |
| MPV17 | MpV17 mitochondrial inner membrane protein |
| MSRA | methionine sulfoxide reductase A |
| MTL5 | metallothionein-like 5 |
| NCF1 | neutrophil cytosolic factor 1 |
| NCF2 | neutrophil cytosolic factor 2 |
| NOX4 | NADPH oxidase 4 |
| NQO1 | NAD(P)H dehydrogenase, quinone 1 |
| NUDT1 | nudix (nucleoside diphosphate linked moiety X)-type motif 1 |
| OXR1 | oxidation resistance 1 |
| OXSR1 | oxidative-stress responsive 1 |
| PDLIM1 | PDZ and LIM domain 1 (elfin) |
| PNKP | polynucleotide kinase 3'-phosphatase |
| PON1 | paraoxonase 1 |
| PPID | peptidylprolyl isomerase D (cyclophilin D) |
| PRDX1 | peroxiredoxin 1 |
| PRDX2 | peroxiredoxin 2 |
| PRDX3 | peroxiredoxin 3 |
| PRDX4 | peroxiredoxin 4 |
| PRDX5 | peroxiredoxin 5 |
| PRDX6 | peroxiredoxin 6 |
| PREX1 | phosphatidylinositol 3,4,5-trisphosphate-dependent RAC exchanger 1 |
| PRG3 | proteoglycan 3 |
| PRNP | prion protein (p27-30) |
| PTGS1 | prostaglandin-endoperoxide synthase 1 |
| PTGS2 | prostaglandin-endoperoxide synthase 2 |
| RNF7 | ring finger protein 7 |
| SCARA3 | scavenger receptor class A, member 3 |
| SELS | selenoprotein S |
| SERPINH1 | serpin peptidase inhibitor, clade H (heat shock protein 47), member 1 |
| SFTPD | surfactant, pulmonary-associated protein D |
| SGK2 | serum/glucocorticoid regulated kinase 2 |
| SIRT2 | sirtuin 2 |
| SOD1 | superoxide dismutase 1 |
| SOD2 | superoxide dismutase 2 |
| SQSTM1 | sequestosome 1 |
| SRXN1 | sulfiredoxin 1 |
| ST13 | suppression of tumorigenicity 13 |
| STK25 | serine/threonine kinase 25 |
| TCP1 | t-complex 1 |
| TTN | titin |
| TXNRD1 | thioredoxin reductase 1 |
| TXNRD2 | thioredoxin reductase 2 |
| UCP2 | uncoupling protein 2 |

TABLE 3

21-gene signature

| Gene symbol | Gene title | Weight |
|---|---|---|
| CSDE1 | cold shock domain containing E1, RNA-binding | 1 |
| DNAJC8 | DnaJ (Hsp40) homolog, subfamily C, member 8 | 1 |
| DNAJB9 | DnaJ (Hsp40) homolog, subfamily B, member 9 | 1 |
| PRDX5 | peroxiredoxin 5 | 1 |
| GCLM | glutamate-cysteine ligase, modifier subunit | 1 |
| DNAJA3 | DnaJ (Hsp40) homolog, subfamily A, member 3 | −1 |
| CCT7 | chaperonin containing TCP1, subunit 7 (eta) | −1 |
| GSTP1 | glutathione S-transferase pi | −1 |
| FTH1 | ferritin, heavy polypeptide 1 | −1 |
| NCF1 | neutrophil cytosolic factor 1 | −1 |
| CCT8 | chaperonin containing TCP1, subunit 8 (theta) | −1 |
| CYBA | cytochrome b-245, alpha polypeptide | −1 |
| DNAJB11 | DnaJ (Hsp40) homolog, subfamily B, member 11 | −1 |
| PRDX2 | peroxiredoxin 2 | −1 |
| GSR | glutathione reductase | −1 |
| HSPA1A | heat shock 70 kDa protein 1A | −1 |
| DNAJC5 | DnaJ (Hsp40) homolog, subfamily C, member 5 | −1 |
| SOD2 | superoxide dismutase 2 | −1 |
| PRDX3 | peroxiredoxin 3 | −1 |
| DNAJB6 | DnaJ (Hsp40) homolog, subfamily B, member 6 | −1 |
| KEAP1 | kelch-like ECH-associated protein 1 | −1 |

Discussion

Oxidative stress plays an important role in the pathogenesis of sepsis and decreases survival yet reliable ROS-associated biomarkers for predicting survival and assessing response to therapy in sepsis are lacking. We report the first ROS-associated, PBMC-derived novel gene expression signature for predicting survival in sepsis. This 21-gene signature was identified from approximately 1500 differentially expressed genes in PBMCs of sepsis non-survivors in a discovery cohort and 137 preselected ROS-associated genes. It was validated in an independent cohort and predicts survival in sepsis.

The strengths of our analysis include a robust methodology for identification of the differentially-expressed genes in PBMCs that are associated with survival in patients with sepsis, confirmation of this signature as a significant predictor of mortality in sepsis in an independent cohort, and the use of survival as the main outcome.

REFERENCES

1. Salvo, I., et al., *The Italian SEPSIS study: preliminary results on the incidence and evolution of SIRS, sepsis, severe sepsis and septic shock.* Intensive Care Med, 1995. 21 Suppl 2: p. S244-9.
2. Levy, M. M., et al., *2001 SCCM/ESICM/ACCP/ATS/SIS International Sepsis Definitions Conference.* Crit Care Med, 2003. 31(4): p. 1250-6.
3. Victor, V. M., et al., *Oxidative stress and mitochondrial dysfunction in sepsis: a potential therapy with mitochondria-targeted antioxidants.* Infect Disord Drug Targets, 2009. 9(4): p. 376-89.
4. Galley, H. F., *Oxidative stress and mitochondrial dysfunction in sepsis.* Br J Anaesth, 2011. 107(1): p. 57-64.
5. Macdonald, J., H. F. Galley, and N. R. Webster, *Oxidative stress and gene expression in sepsis.* Br J Anaesth, 2003. 90(2): p. 221-32.
6. Quoilin, C., et al., *Evidence of oxidative stress and mitochondrial respiratory chain dysfunction in an in vitro model of sepsis-induced kidney injury.* Biochim Biophys Acta, 2014. 1837(10): p. 1790-800.
7. Galley, H. F., *Bench-to-bedside review: Targeting antioxidants to mitochondria in sepsis.* Crit Care, 2010. 14(4): p. 230.
8. Zhang, Y. and N. Kaminski, *Biomarkers in idiopathic pulmonary fibrosis.* Curr Opin Pulm Med, 2012. 18(5): p. 441-6.
9. Selman, M., et al., *Gene expression profiles distinguish idiopathic pulmonary fibrosis from hypersensitivity pneumonitis.* Am J Respir Crit Care Med, 2006. 173(2): p. 188-98.
10. Boon, K., et al., *Molecular phenotypes distinguish patients with relatively stable from progressive idiopathic pulmonary fibrosis (IPF).* PLoS One, 2009. 4(4): p. e5134.
11. Konishi, K., et al., *Gene expression profiles of acute exacerbations of idiopathic pulmonary fibrosis.* Am J Respir Crit Care Med, 2009. 180(2): p. 167-75.
12. Pandit, K. V., et al., *Inhibition and role of let-7d in idiopathic pulmonary fibrosis.* Am J Respir Crit Care Med, 2010. 182(2): p. 220-9.
13. Pandit, K. V., J. Milosevic, and N. Kaminski, *MicroRNAs in idiopathic pulmonary fibrosis.* Transl Res, 2011. 157(4): p. 191-9.
14. Navab, R., et al., *Prognostic gene-expression signature of carcinoma-associated fibroblasts in non-small cell lung cancer.* Proc Natl Acad Sci USA, 2011. 108(17): p. 7160-5.
15. Shedden, K., et al., *Gene expression-based survival prediction in lung adenocarcinoma: a multi-site, blinded validation study.* Nat Med, 2008. 14(8): p. 822-7.
16. Pitroda, S. P., et al., *Tumor endothelial inflammation predicts clinical outcome in diverse human cancers.* PLoS One, 2012. 7(10): p. e46104.
17. Herazo-Maya, J. D., et al., *Peripheral blood mononuclear cell gene expression profiles predict poor outcome in idiopathic pulmonary fibrosis.* Sci Transl Med, 2013. 5(205): p. 205ra136.
18. Desai, A. A., et al., *A novel molecular signature for elevated tricuspid regurgitation velocity in sickle cell disease.* Am J Respir Crit Care Med, 2012. 186(4): p. 359-68.
19. Kiliszek, M., et al., *Altered gene expression pattern in peripheral blood mononuclear cells in patients with acute myocardial infarction.* PLoS One, 2012. 7(11): p. e50054.
20. Zhou, T., et al., *Peripheral blood gene expression as a novel genomic biomarker in complicated sarcoidosis.* PLoS One, 2012. 7(9): p. e44818.
21. Zhou, T., T. Wang, and J. G. Garcia, *A nonmuscle myosin light chain kinase-dependent gene signature in peripheral blood mononuclear cells is linked to human asthma severity and exacerbation status.* Pulm Circ, 2015. 5(2): p. 335-8.
22. Zhou, T., T. Wang, and J. G. Garcia, *Expression of nicotinamide phosphoribosyltransferase-influenced genes predicts recurrence free survival in lung and breast cancers.* Sci Rep, 2014. 4: p. 6107.
23. Zhou, T., T. Wang, and J. G. Garcia, *Genes influenced by the non-muscle isoform of Myosin light chain kinase impact human cancer prognosis.* PLoS One, 2014. 9(4): p. e94325.
24. Parnell, G. P., et al., *Identifying key regulatory genes in the whole blood of septic patients to monitor underlying immune dysfunctions.* Shock, 2013. 40(3): p. 166-74.
25. Tsalik, E. L., et al., *An integrated transcriptome and expressed variant analysis of sepsis survival and death.* Genome Med, 2014. 6(11): p. 111.
26. Kanehisa, M., et al., *The KEGG resource for deciphering the genome.* Nucleic Acids Res, 2004. 32(Database issue): p. D277-80.
27. Huang da, W., B. T. Sherman, and R. A. Lempicki, *Systematic and integrative analysis of large gene lists using DAVID bioinformatics resources.* Nat Protoc, 2009. 4(1): p. 44-57.
28. Dennis, G., Jr., et al., *DAVID: Database for Annotation, Visualization, and Integrated Discovery.* Genome Biol, 2003. 4(5): p. P3.
29. Ashburner, M., et al., *Gene ontology: tool for the unification of biology. The Gene Ontology Consortium.* Nat Genet, 2000. 25(1): p. 25-9.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:
1. A method of determining a risk of death from sepsis by detecting altered gene expression in a subject with sepsis, comprising:
  a) obtaining a sample from said subject wherein the sample is selected from the group consisting of whole blood, plasma, serum, and urine; and
  b) detecting the level of expression of CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, and KEAP1 by performing polymerase chain reaction on the sample and detecting amplified nucleic acids in the sample; and c) comparing said level of gene expression in said subject with sepsis to the level in a subject without sepsis;

d) calculating a risk score as a linear combination of expression values of said genes, wherein a positive number score is indicative of said subject being at risk of death from sepsis;

e) treating the subject for sepsis;

f) obtaining a biological sample from the subject after treatment for sepsis;

g) determining gene expression levels of CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, and KEAP1 in the biological sample obtained after treatment for sepsis by performing polymerase chain reaction on the sample and detecting amplified nucleic acids in the sample;

h) calculating a risk score as a linear combination of expression values of said genes in the subject after treatment for sepsis; and i) determining the treatment as a favorable treatment if the risk score decreases after treatment.

2. The method of claim 1, wherein each risk score is calculated using the formula:

$$S = \sum_{i=1}^{n} W_i(e_i - \mu_i)/\tau_i,$$

where S is the risk score of the patient; n is 21 and represents the number of genes in claim 1; $W_i$ denotes the weight of gene i as shown in Table 2; $e_i$ denotes the expression level of gene i; and $\mu_i$ and $\tau_i$ are the mean and standard deviation of the gene expression values for gene i across all samples, respectively.

3. A method of monitoring the treatment of sepsis in a human subject, the method comprising:

obtaining a biological sample from a subject being treated for sepsis;

determining gene expression levels of CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, and KEAP1 in the biological sample by performing polymerase chain reaction on the sample and detecting amplified nucleic acids in the sample;

comparing the gene expression levels to reference gene expression levels, wherein the reference gene expression levels are gene expression levels of CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, and KEAP1 for one or more of subjects not having sepsis and subjects having non-life threatening sepsis; and calculating a risk score as a linear combination of expression values of said genes in the subject being treated for sepsis and identifying the treatment as a favorable treatment response if the risk score of the subject being treated for sepsis is about the same as a risk score calculated from one or more of subjects not having sepsis and subjects having non-life threatening sepsis;

treating the subject for sepsis;

obtaining a biological sample from the subject after treatment for sepsis;

determining gene expression levels of CSDE1, DNAJC8, DNAJB9, PRDX5, GCLM, DNAJA3, CCT7, GSTP1, FTH1, NCF1, CCT8, CYBA, DNAJB11, PRDX2, GSR, HSPA1A, DNAJC5, SOD2, PRDX3, DNAJB6, and KEAP1 in the biological sample obtained after treatment for sepsis by performing polymerase chain reaction on the sample and detecting amplified nucleic acids in the sample;

calculating a risk score as a linear combination of expression values of said genes in the subject after treatment for sepsis; and determining the treatment as a favorable treatment if the risk score decreases after treatment.

4. The method of claim 3, wherein the biological sample comprises peripheral blood mononuclear cells.

5. The method of claim 3, further comprising communicating the effectiveness of the treatment to the subject or a health care provider.

6. The method of claim 3, wherein each risk score is calculated using the formula:

$$S = \sum_{i=1}^{n} W_i(e_i - \mu_i)/\tau_i,$$

where S is the risk score of the patient; n is 21; $W_i$ denotes the weight of gene i as shown in Table 2; $e_i$ denotes the expression level of gene i; and $\mu_i$ and $\tau_i$ are the mean and standard deviation of the gene expression values for gene i across all samples, respectively.

7. The method of claim 1, wherein the biological sample comprises peripheral blood mononuclear cells.

8. The method of claim 1, further comprising communicating the effectiveness of the treatment to the subject or a health care provider.

* * * * *